United States Patent [19]

King

[11] 4,189,387
[45] Feb. 19, 1980

[54] LUBRICANT COMPOSITIONS BASED ON ZIRCONIUM POLYMERS

[76] Inventor: James P. King, 904 Breezewood La., Lansdale, Pa. 19446

[21] Appl. No.: 938,459

[22] Filed: Aug. 31, 1978

[51] Int. Cl.$^2$ .................. C10M 5/24; C10M 5/22; C10M 5/14; C10M 7/46
[52] U.S. Cl. .................. 252/32.7 E; 252/32.5; 252/33.6; 252/35; 252/37.7
[58] Field of Search .................. 252/32.5, 32.7 E, 35, 252/37.7, 33.6

[56] References Cited

U.S. PATENT DOCUMENTS

| | | | |
|---|---|---|---|
| 2,681,922 | 6/1954 | Balthis | 252/37.7 |
| 3,030,320 | 4/1962 | Haslam | 252/35 |
| 3,262,881 | 7/1966 | Ravner et al. | 252/37.7 |
| 3,490,737 | 1/1970 | Gieseking et al. | 252/37.7 |

*Primary Examiner*—Irving Vaughn

[57] ABSTRACT

This invention deals with new lubricant compositions comprising a liquid lubricant thickened with a zirconium polymer containing a bridged zirconium atom where the bridged groups are the anions of phosphinic acids of structure RR'P(X)XH or of carboxylic acids of structure RCOOH where R and R' are selected from hydrogen, alkyl, aryl, fluorinated and perfluorinated alkyl and aryl groups and X is oxygen or sulfur.

8 Claims, No Drawings

LUBRICANT COMPOSITIONS BASED ON ZIRCONIUM POLYMERS

This invention relates to improved lubricant compositions and, more particularly, improved greases.

It has previously been disclosed that greases may be prepared from various fluids such as described in U.S. Pat. Nos. 3,331,774, 3,331,775, 3,332,873 and 3,522,178 by thickening such fluids with inorganic polymers based on chromium, iron, ruthenium, europium and ytterbium centers.

I have now discovered that fluid lubricants can be thickened with zirconium polymers having a bridged zirconium atom wherein the bridged groups are the anions of phosphinic acids of the structure RR'P(X)XH or of carboxylic acids of the structure RCOOH wherein R and R' are selected from the group of hydrogen, alkyl, aryl, fluorinated and perfluorinated alkyl, and aryl groups and X is oxygen or sulfur.

The lubricant compositions based on the zirconium polymers of this invention are colorless and easily prepared, show excellent thermal stability, being in the order of from 500 to 900° F., and have excellent properties with respect to consistency, drop point, oil separation, oxidation stability, wear prevention characteristics and load carrying capacity. The thickened products range from viscous paste to grease-like texture depending on fluid-thickener combination, thickener concentration and number of hydroxy groups per zirconium atom.

The fluids to be thickened include mineral oil, silicones, fluorinated silicones, perfluoropolyethers, esters, and synthetic hydrocarbons. Most advantageous thickener concentrations range from 6 to 35 wt. percent.

The lubricant composition of this invention may be prepared by a number of known methods for preparing greases. The preferred method is to react a freshly precipitated and wet zirconium hydroxide [$ZrO(OH)_2 \cdot XH_2O$] with an acid or mixture of acids suspended or dissolved in the fluid to be thickened, heated with agitation to about 70°–120° C., preferably 70°–90° C. cooled to about 80°–95° C. and held at this temperature until reaction is complete, i.e. for 10–30 minutes depending upon the acid employed. The resulting mass is agitated with a Z-blade or similar stirrer for about 50–70 minutes at 90°–110° C. Any water separating is decanted off and the thickened product is cured for about 1–2 hours or until a constant weight is obtained, at a temperature of 100°–160° C.

The following Examples illustrate how the invention may be practiced, although it should be understood that variations therein may be made within the scope of the invention.

EXAMPLE 1

Preparation of $Zr_4O_4(OH)_{7.5}[OP(CH_2CH_2C_9F_{19})_2O]_{0.5}$-Perfluoropolyether Grease A solution of 25.8 g (0.08 m) of $ZrOCl_2 \cdot 8H_2O$ in 250 ml distilled water was treated slowly with 160 g of 2 N $NH_4OH$ solution under vigorous agitation. A white precipitate was deposited, collected by filtration and washed repeatedly with distilled water. The semi-dry solid (complete dry of this precipitate should be avoided to prevent it from converting to $ZrO_2 \cdot XH_2O$) was immediately added to an acid-fluid mixture of 10.6 g (0.01 m) of $(C_9F_{19}CH_2CH_2)_2P(O)OH$ and 51.2 g of perfluorinated alkyl ether fluid at 90° C. The acid-fluid mixture was first heated up to 110° with agitation, then allowed to cool to 90° C. and held at this temperature until reaction was completed, i.e. about 15 minutes. The resulting mass was slowly agitated with a Z-blade stirrer and heated between 90° and 110° C. for about 60 minutes to give a stiff paste. A small amount of water was separated and decanted off during this heating period. The thickened product was then transferred to a beaker and cured at 150° C. in a forced air oven for about two hours, until constant weight (71 g) was obtained followed by milling on a three-roll mill. The physical properties and performance data are recorded in Table I.

EXAMPLE 2

Preparation of $Zr_4O_4(OH)_7[OP(CH_2CH_2C_9F_{19})(Ph)O]$-Perfluoropolyether Grease As in Example 1, a solution of 51.5 g (0.16 m) of $ZrOCl_2 \cdot 8H_2O$ in 300 ml $H_2O$ was treated with 352 g of 2 N $NH_4OH$ solution. The precipitate was isolated and allowed to react with 25.5 g (0.04 m) of $(C_9F_{19}CH_2CH_2)(Ph)P(O)OH$ suspended in 110.4 g of perfluoropolyether fluid at 90° C. in the same manner as described in Example 1. Evaluation results on the thickened product (151 g) are listed in Table I.

EXAMPLE 3

Preparation of $Zr_4O_4(OH)_7(OOCC_{10}F_{21})$-Perfluoropolyether Grease

A solution of 64 g (0.2 m) of $ZrOCl_2 \cdot 8H_2O$ in 400 ml distilled water was treated, as in Example 1, with 440 g of 2 N $NH_4OH$ solution resulting in formation of a white precipitate which was isolated and allowed to react with 28.2 g (0.05 m) of $C_{10}F_{21}COOH$ dissolved in 131 g of perfluoropolyether fluid between 90° and 100° C. as described in Example 1. The thickened product was so stiff that an additional 26 g of the fluid was added followed by curing at 150° C. for two hours and milling on a three-roll mill. The evaluation results of the final product (204 g) are recorded in Table I.

EXAMPLE 4

Preparation of $Zr_4O_4(OH)_7(OOCC_{10}F_{21})$-Fluorinated Polysiloxane Grease

A solution of 38.6 g (0.12 m) of $ZrOCl_2 \cdot 8H_2O$ in 300 ml distilled water was treated with 240 g of 2 N $NH_4OH$ solution with vigorous agitation resulting in instant formation of a white precipitate of $ZrO(OH)_2 \cdot XH_2O$ which was collected by filtration, washed repeatedly with distilled water and kept from complete drying until use. A sample of 16.9 g (0.03 m) of $C_{10}F_{21}COOH$ was dissolved in 78.6 g of fluorinated polysiloxane fluid by heating up the mixture between 100° and 110° C. The freshly precipitated and wet $ZrO(OH)_2 \cdot XH_2O$ was then introduced into the acid-fluid solution at 90° C. The resulting mass was heated and agitated for 60 minutes in a 110° C. oil bath; a small amount of water was separated from the reaction mixture and decanted off. The thickened product was transferred to a beaker, cured at 150° C. until constant weight and milled on a three-roll mill for several times. The evaluation data of the thickened product (102 g) are listed in Table II.

EXAMPLE 5

Preparation of
$Zr_4O_4(OH)_{7.5}[OP(CH_2CH_2C_9F_{19})(Ph)O]_{0.5}$-
Fluorinated Polysiloxane Grease Freshly precipitated $ZrO(OH)_2 \cdot XH_2O$, prepared from 64.4 g (0.2 m) of $ZrOCl_2 \cdot 8H_2O$ and 440 g of 2 N $NH_4OH$ solution, was allowed to react with 15.9 g (0.025 m) of $(C_9F_{19}CH_2CH_2)(Ph)P(O)OH$ suspended in 83 g of fluorinated polysiloxane. The thickened product was produced by using the same procedure as described in Example 4. The product (121 g) was subjected to preliminary evaluation and the results are recorded in Table II.

EXAMPLE 6

Preparation of $Zr_4O_4(OH)_4[OP(Me)(Ph)O]_4$-High Phenyl Content Polysiloxane Grease A solution of 32.2 g (0.1 m) of $ZrOCl_2 \cdot 8H_2O$ in 200 ml water was treated with 200 g of 2 N $NH_4OH$ solution and the freshly precipitated zirconyl hydroxide was collected by filtration, washed repeatedly with distilled water and kept from complete drying. A sample of 15.6 g (0.1 m) of $Me(Ph)P(O)OH$ was suspended in 68.5 g of high phenyl content polysiloxane fluid by heating the acid-fluid mixture up to 140° C. with agitation. The suspension was allowed to cool to below 100° C. followed by reaction with the freshly precipitated zirconyl hydroxide. The resulting mass was slowly heated up to 150° C. and held at that temperature for 45 minutes with continuous and slow agitation. Any water that was separated from the reaction mixture during this heating period was decanted off. The thickened product was heated in a forced air oven at 150° C. for two hours or to constant weight followed by curing at 260° C. for two hours and milling on a three-roll mill. Evaluation data of the product (89 g) are recorded in Table III.

EXAMPLE 7

Preparation of $Zr_4O_4(OH)_4[OPPh_2O]_4$-High Phenyl Content Polysiloxane Grease Samples consisting of 51.5 g (0.16 m) of $ZrOCl_2 \cdot 8H_2O$, 34.9 g (0.16 m) of $Ph_2P(O)OH$, and 127 g of high phenyl content polysiloxane were used to prepare $Zr_4O_4(OH)_4(OPPh_2O)_4$-polysiloxane grease (170 g) with the same procedure as described in Example 6. Evaluation data are recorded in Table III.

Table I.

Evaluation Results of Greases Based on Perfluoropolyether Fluid (MCO 66-18) Thickened with Various Zirconium Polymers

| | Base Fluid* | Example 1 | Example 2 | Example 3 |
|---|---|---|---|---|
| Thickener | | $Zr_4O_4(OH)_{7.5}[OP(CH_2-CH_2C_9F_{19})_2O]_{0.5}$ | $Zr_4O_4(OH)_7[OP(CH_2-CH_2C_9F_{19})(Ph)O]$ | $Zr_4O_4(OH)_7(OOC_{10}F_{21})$ |
| Weight Percent of Thickener | | 30 | 30 | 26 |
| Penetration (ASTM D 1403) | | | | |
| Unworked (Conv. to D 217) | | 238 | 279 | 290 |
| Worked (Conv. to D 217) | | 260 | 237 | 298 |
| Drop Point (ASTM D 566), °F. | | >464 | 454 | >464 |
| Oil Separation (FTMS 791-321) | | | | |
| Weight Percent after 30 h at 400° F. | | 4.0 | 5.4 | 7.3 |
| Oxilation Stability (ASTM D 942) | | | | |
| Psig $O_2$ pressure drop in 600 h, 210° F. | | 0 | 0 | 0 |
| Extreme Pressure Properties (ASTM D 2596) | | | | |
| Weld Point, kg (AISI-C-52100 steel) | 400 | 470 | >620 | 500 |
| Wear Prevention Characteristics (ASTM D 2266) | | | | |
| 40 kg load, 1200 rpm, 167° F. and 1 h | | | | |
| Scar diameter, mm (AISI-C-52100 steel) | 1.09 | 0.49 | 0.56 | 0.53 |

*Perfluoropolyether fluid; 100° F. viscosity, 270 cs; density, 1.890 g/cc at 77° F.; temperature range, −30° to 650° F.

Table II.

Evaluation Results of Greases Based on Fluorinated Polysiloxane Fluid Thickened with Various Zirconium Polymers

| | Base Fluid* | Example 4 | Example 5 |
|---|---|---|---|
| Thickener | | $Zr_4O_4(OH)_7(OOCC_{10}F_{21})$ | $Zr_4O_4(OH)_{7.5}[OP(CH_2CH_2C_9F_{19})(Ph)O]_{0.5}$ |
| Weight Percent of Thickener | | 30 | 30 |
| Penetration (ASTM D 1403) | | | |
| Unworked (Conv. to D 217) | | 204 | 174 |
| Worked (Conv. to D 217) | | 215 | 215 |
| Drop Point (ASTM D 566), °F. | | >464 | >464 |
| Oil Separation (FTMS 791-321) | | | |
| Weight Percent after 30 h at 400° F. | | 1.2 | 1.0 |
| Oxidation Stability (ASTM D 942) | | | |
| Psig $O_2$ pressure drop in 600 h, 210° F. | | 0 | 0 |
| Extreme Pressure Properties (ASTM D 2596) | | | |
| Weld Point, kg (AISI-C-52100 steel) | 126 | 200 | 200 |
| Wear Prevention Characteristics (ASTM D 2266) | | | |
| 40 kg load, 1200 rpm, 167° F. and 1 h | | | |
| Scar diameter, mm (AISI-C-52100 steel) | 1.26 | 1.42 | 1.52 |

*Fluorinated polysiloxane fluid; 100° F. viscosity, 75 cs; density, 1.150 g/cc at 77° F.; temperature range, −65° to +400° F.

Table III.

Evaluation Results of Greases Based on High Phenyl Content Polysiloxane Thickeners with Various Zirconium Polymers

|  | Base Fluid* | Example 6 | Example 7 |
|---|---|---|---|
| Thickener |  | $Zr_4O_4(OH)_4[OP(Me)(Ph)O]_4$ | $Zr_4O_4(OH)_4[OPPh_2O]_4$ |
| Weight Percent of Thickener |  | 30 | 30 |
| Penetration (ASTM D 1403) |  |  |  |
| Unworked (Conv. to D 217) |  | 275 | 339 |
| Worked (Conv. to D 217) |  | 282 | 372 |
| Drop Point (ASTM D 566), °F. |  | >464 | 410 |
| Oil Separation (FTMS 791-321) |  |  |  |
| Weight Percent after 30 h at 400° F. |  | 2.8 | 5.6 |
| Oxidation Stability (ASTM D 942) |  |  |  |
| Psig $O_2$ pressure drop in 600 h, 210° F. |  | 0 | 0 |
| Extreme Pressure Properties (ASTM D 2596) |  |  |  |
| Weld Point, kg (AISI-C-52100 steel) | 126 | 282 | 315 |
| Wear Prevention Characteristics (ASTM D 2266) |  |  |  |
| 40 kg load, 1200 rpm, 167° F. and 1 h |  |  |  |
| Scar diameter, mm (AISI-C-52100 steel) | 3.75 | 2.44 | 3.15 |

*High phenyl content polysiloxane; viscosity at 100° F., 240 cs; density at 77° F., 1.106 g/cc; temperature range +25° to 650° F.

I claim:

1. A lubricant composition comprising a liquid lubricant thickened with a zirconium polymer having a structural formula selected from the group consisting of $$[Zr_4O_4(OH)_{8-y}(XPRR'X)_y]_n$$

and $$[Zr_4O_4(OH)_{8-y}(OOCR)_y]_n$$

where

R and R' are hydrogen, alkyl, aryl, fluorinated and perfluorinated alkyl and aryl groups;

X is oxygen or sulfur;

y is equal to 0.1 to 7.9; and n is ranging from 2 to 30.

2. A lubricant composition of claim 1 comprising a liquid lubricant thickened with a zirconium polymer having a bridged zirconium atom wherein the bridged groups contained therein are the anions of an acid selected from the group consisting of phosphinic acid of the structure RR'P(X)XH and carboxylic acids of the structure

RCOOH wherein

R and R' are hydrogen, alkyl, aryl, fluorinated and perfluorinated alkyl and aryl groups;

X is oxygen or sulfur;

y is equal to 0.1 to 7.9; and n is ranging from 2 to 30.

3. The product of claim 1 wherein the liquid lubricant is a mineral oil.

4. The product of claim 1 wherein the liquid lubricant is a silicone.

5. The product of claim 1 wherein the liquid lubricant is a perfluoroalkyl ether.

6. The product of claim 1 wherein the liquid lubricant is a fluorinated polysiloxane.

7. The product of claim 1 wherein the liquid lubricant is a synthetic ester or hydrocarbon.

8. A process for the preparation of a lubricating composition which comprises mixing a freshly precipitated and wet zirconium hydroxide [$ZrO(OH)_2 \cdot XH_2O$] with a phosphinic acid of the structure RR'P(X)XH or of a carboxylic acid of the structure RCOOH wherein R and R' are selected from the group of hydrogen, alkyl, aryl, fluorinated and perfluorinated alkyl, and aryl groups and X is oxygen or sulfur, said acid being suspended or dissolved in the fluid lubricant to be thickened and heating the resultant mixture, with agitation, in the range of 70° to 99° C. and then allowing it to cool to about 80° C. and holding the mixture at this temperature for 60 minutes following which the resulting mass is slowly agitated at 90°-110° C. for about an hour and then curing the resultant product at about 110° to 150° C. for about two hours until a constant weight is obtained.

* * * * *

UNITED STATES PATENT AND TRADEMARK OFFICE
CERTIFICATE OF CORRECTION

PATENT NO. : 4,189,387
DATED : February 19, 1980
INVENTOR(S) : James P. King

It is certified that error appears in the above—identified patent and that said Letters Patent is hereby corrected as shown below:

On The Title Page Insert:

--[73] Assignee: Pennwalt Corporation, Philadelphia, Pennsylvania --.

Signed and Sealed this

Fourteenth Day of October 1980

[SEAL]

Attest:

SIDNEY A. DIAMOND

Attesting Officer     Commissioner of Patents and Trademarks